US007252085B2

(12) United States Patent
Kunschir

(10) Patent No.: US 7,252,085 B2
(45) Date of Patent: Aug. 7, 2007

(54) DEVICE FOR INHALATION THERAPY

(75) Inventor: Eduard Kunschir, Munich (DE)

(73) Assignee: Pari GmbH Spezialisten fur Effektive Inhalation (DE)

( * ) Notice: Subject to any disclaimer, the term of this patent is extended or adjusted under 35 U.S.C. 154(b) by 131 days.

(21) Appl. No.: 10/810,098

(22) Filed: Mar. 26, 2004

(65) Prior Publication Data

US 2005/0056274 A1 Mar. 17, 2005

Related U.S. Application Data

(63) Continuation of application No. PCT/EP02/011706, filed on Oct. 18, 2002.

(51) Int. Cl.
*A61M 15/00* (2006.01)

(52) U.S. Cl. .................................................. 128/200.16

(58) Field of Classification Search ........... 128/200.14, 128/203.12, 200.21, 200.16, 200.23, 203.15, 128/203.21, 204.23
See application file for complete search history.

(56) References Cited

U.S. PATENT DOCUMENTS 4,091,297 A 5/1978 Stephens ..................... 327/95
4,300,131 A * 11/1981 Mitsui et al. ............... 340/618
4,414,512 A 11/1983 Nelson ........................ 327/93
4,533,082 A * 8/1985 Maehara et al. ............... 239/4
4,775,808 A 10/1988 Trumpp ....................... 326/34
4,790,479 A 12/1988 Matsumoto et al. ..... 239/102.2
4,866,301 A 9/1989 Smith .......................... 327/60
5,152,456 A * 10/1992 Ross et al. ............... 239/102.2
5,159,340 A 10/1992 Smith .......................... 341/132
5,261,601 A * 11/1993 Ross et al. ............... 239/102.2
5,272,394 A 12/1993 Kirk et al. ..................... 327/58
5,440,244 A 8/1995 Richter et al. ................ 326/37
5,487,378 A * 1/1996 Robertson et al. ..... 128/200.16
5,512,853 A 4/1996 Ueno et al. ................. 327/333
5,933,026 A 8/1999 Larsen et al. ................. 326/81
6,152,130 A * 11/2000 Abrams et al. ........ 128/204.21
6,242,949 B1 6/2001 Wilford ....................... 326/81
6,402,046 B1 * 6/2002 Loser ............................ 239/4

FOREIGN PATENT DOCUMENTS

| | | |
|---|---|---|
| DE | 199 62 280 | 7/2001 |
| EP | 0 051 343 | 5/1982 |
| EP | 0 844 736 | 11/1996 |
| EP | 1 092 446 | 4/2001 |
| WO | 98/28846 | 7/1998 |

* cited by examiner

*Primary Examiner*—Steven O. Douglas
(74) *Attorney, Agent, or Firm*—Merchant & Gould P.C

(57) ABSTRACT

The invention relates to a device for inhalation therapy. Said device comprises an aerosol-producing device for spraying a liquid (3), preferably comprising a membrane (1), a support unit (6), an electromechanical transducer unit (7), and a connecting device (8,9) for supplying an oscillation control signal. The inventive device also comprises a control device (10) from which an oscillation control signal can be supplied to the connecting device of the aerosol-producing device, such that the aerosol-producing device sprays the liquid. Another control signal is supplied to the aerosol-producing device (1,6,7), moving the membrane (1) in oscillation in an audible frequency range, thus causing the emission of audible signals for a user.

7 Claims, 1 Drawing Sheet

DEVICE FOR INHALATION THERAPY

This application is a continuation of international application number PCT/EP2002/011706, filed 18 Oct. 2002.

BACKGROUND OF THE INVENTION

The invention relates to devices for inhalation therapy having an aerosol generator, in particular with an oscillatable membrane for nebulising a liquid or powder.

BRIEF SUMMARY OF THE INVENTION

Devices for inhalation therapy having a controllable aerosol generator need to signal different operating states of the device to the patient. Indicator elements such as light emitting diodes or sound signal generators have been used to date for this purpose, by means of which the beginning and end of a therapy session, for example, or other information is indicated to the patient.

The invention shows a way in which acoustic signals can be emitted in a device for inhalation therapy without additional sound signal generators, for example to indicate specific operating states of the device to the patient.

This is achieved according to the invention by means of a device for inhalation therapy comprising an oscillatable membrane for nebulisiug a liquid, an oscillation generating device which has at least one connecting means for receiving an oscillation control signal and by means of which the membrane is caused to oscillate when the oscillation control signal is supplied such that a liquid disposed on one side of the membrane is nebulised through the membrane and is present on the other side of the membrane as an aerosol, and comprising a control means from which an oscillation control signal can be supplied to the at least one connecting means of the oscillation generating device such that the oscillation generating device causes the membrane to oscillate, with the control means being designed such that a further control signal of the control means can be supplied to the oscillation generating device, said further signal causing the membrane to oscillate in the audible frequency range so as to emit an audible signal for a user.

The invention is based on the in fact surprising realisation that in membrane nebulisers, the electromechanical transducer unit used to cause oscillation, generally a piezoelectric component, can also be caused to oscillate in the audible frequency range and the nebuliser membrane then functions as an electroacoustic transducer (signal generator) without nebulisation being impaired. It is also surprising that sufficiently high signal levels can be achieved, specifically also during the nebulising operation.

The solution according to the invention is basically suitable for all devices for inhalation therapy in which a controlled aerosol generator is used that is able to emit an audible sound signal when a corresponding control signal is supplied. The applicability of the invention is thus not restricted to membrane nebulisers, even though nebulisers of this type are especially advantageous.

The invention can thus be characterised, even in abstract, as a device for inhalation therapy comprising an aerosol generating device for nebulising a liquid or powder tat has a connecting means for receiving a control signal, and comprising a control means from which a first control signal can be supplied to the connecting means of the aerosol generating device such that the aerosol generating device nebulises the liquid, in which the control means is designed such that a second control signal of the control means can be supplied to the aerosol generating device, said second signal causing an. audible signal for a user to be emitted.

The invention is explained in more detail below by means of an embodiment and referring to the figure showing a schematic representation of a device for inhalation therapy according to the invention.

DETAILED DESCRIPTION

Figure 1:
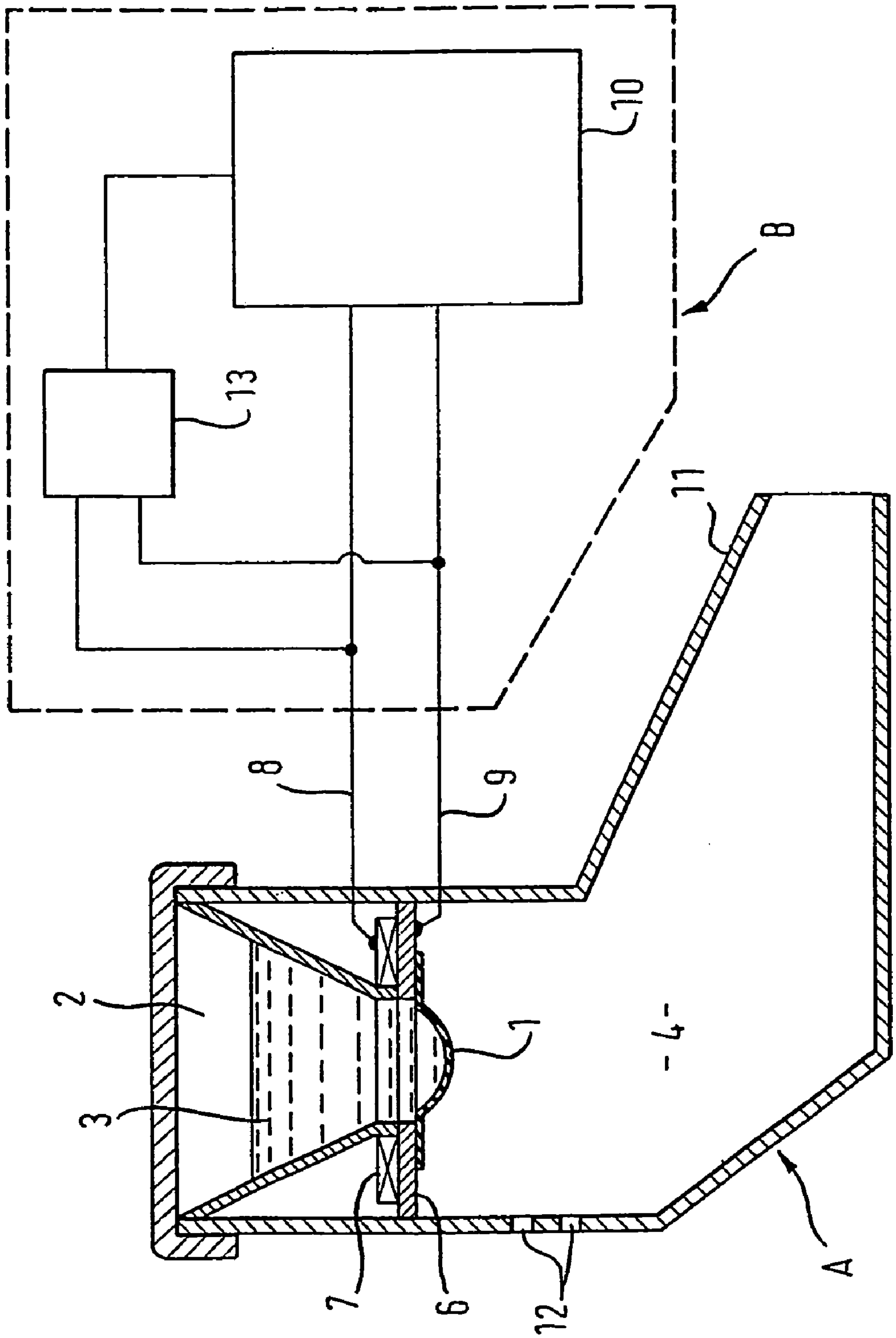
FIG. 1 is a schematic cross-sectional view of device for inhalation therapy according to the invention.

Shown in FIG. 1 is an embodiment of a device for inhalation therapy according to the invention, in which in a nebuliser unit A, a liquid 3 stored in a liquid reservoir 2 is nebulised by means of a membrane 1 into a nebulisation cavity 4. Nebulisation occurs when the membrane 1 is caused to oscillate. For this purpose, the membrane 1 is attached to a support unit 6 which supports the membrane 1 and to which an electromechanical transducer unit 7, for example a piezo element, is also attached. The membrane 1, the support unit 6 and the electromechanical transducer unit 7 are configured in a rotationally symmetrical manner in the embodiment described herein and together form an oscillatable structure. A control signal of a control means 10 can be supplied to the electromechanical transducer unit 7 via connecting lines 8 and 9, said control means 10 being accommodated in a separate control unit B in the embodiment described herein. When the control signal is supplied, the oscillatable structure 1, 6, 7 is caused to oscillate and the liquid 3 is nebulised through the membrane 1.

A patient can inhale the aerosol provided in the nebulisation cavity 4 at the mouthpiece 11 of the nebuliser. So that there is a sufficient supply of air, one or more air holes 12 are provided in the housing of the nebuliser, through which ambient air can enter into the cavity 4 during inhalation and out of which the air inhaled by the patient can exit from the cavity 4 during exhalation.

In order to indicate to the patient that the device for inhalation therapy is in a specific operating state, a further control signal is supplied according to the invention to the oscillatable structure 1, 6, 7. The further control signal causes the membrane 1 to oscillate at an audible frequency such that the membrane 1 emits a sound signal which is audible for the patient. The emission of the sound signal can occur during the nebulisation operation of the membrane 1 without the two oscillations disturbing each other. This is surprising not only since in order to emit an audible sound a frequency in the audible range has to be selected, but also because sufficient energy also has to be supplied to the oscillatable structure 1, 6, 7 so that sound energy can be emitted to a perceptible extent. Nebulisation of the liquid and the quality of the aerosol generated are nevertheless not negatively influenced, particularly since the emission of the sound signal is generally restricted to comparatively short periods.

Therefore, a short sound signal of 0.5 to 2 seconds in length, for example, can be emitted if, following switching on, the optimal operating frequency of the oscillatable structure 1, 6, 7 was found by a search circuit and the membrane is in a steady state. The sound signal can then indicate to the patient that the device for inhalation therapy is ready for operation and that the therapy session can begin. After a specific period or following nebulisation of a predetermined amount of liquid, the end of the therapy session can likewise be signalled by means of a preferably different sounding sound signal. The sound signals are not restricted to mere notes, rather sound sequences or recorded or synthesised voice signals can also be used.

A generator circuit 13 is preferably provided to generate the further control signal, from which the further control signal is supplied to the oscillatable structure 1, 6, 7. The two provided connecting lines 8 and 9 are used for this purpose in the embodiment described herein, via which the oscillation control signal is also supplied to the oscillatable structure 1, 6, 7. The generator unit 13 is advantageously integrated in the control means 10.

The embodiment described in more detail above shows how the generation according to the invention of an acoustic signal for the patient occurs in a device for inhalation therapy having a membrane nebuliser. The description of the embodiment, however, also makes it clear that the invention can be applied to all devices for inhalation therapy in which an aerosol generating device is supplied with a control signal in order to generate an aerosol, and in which an oscillatable structure is used which can cause oscillations in the audible range in addition to the oscillations necessary for nebulisation.

Devices for inhalation therapy in which an electromechanical transducer unit, preferably in the form of a piezoelectric element, is provided are particularly suitable for the use of the invention.

What is claimed is:

1. Device for inhalation therapy, comprising:

a. an oscillatable membrane for nebulising a liquid, b. an oscillation generating device having at least one connecting means, c. a control means, from which a first oscillation control signal is supplied to the at least one connecting means of the oscillation generating device so that said oscillation generating device oscillates the membrane, d. the at least one connecting means receiving the first oscillation control signal for oscillating said membrane when the first oscillation control signal is received such that a liquid disposed on one side of said membrane is nebulised through the membrane and is present on the other side of said membrane as an aerosol, and wherein said control means supplies a further control signal to the oscillation generating device during the first oscillation control signal, such that said oscillation generating device oscillates the membrane in an audible frequency range so as to emit an audible signal for a user.

2. Device for inhalation therapy according to claim 1, wherein the further control signal is supplied to the oscillation generating device via the same connecting means as the first oscillation control signal.

3. Device for inhalation therapy according to claim 1, wherein the oscillation generating device comprises an electromechanical transducer unit, in particular a piezoelectric element.

4. Device for inhalation therapy according to claim 2, wherein the oscillation generating device comprises a support unit to which the electromechanical transducer unit and the membrane are attached.

5. Device for inhalation therapy according to claim 1, wherein a generator unit is provided that generates the further control signal which is supplied to the oscillation generating device via the at least one connecting means.

6. Device for inhalation therapy according to claim 4, wherein the generator unit is integrated in the control means.

7. Device for inhalation therapy claim 1, wherein an energy supply means for the inhalation device is integrated in the control means.

* * * * *